Figure 1:
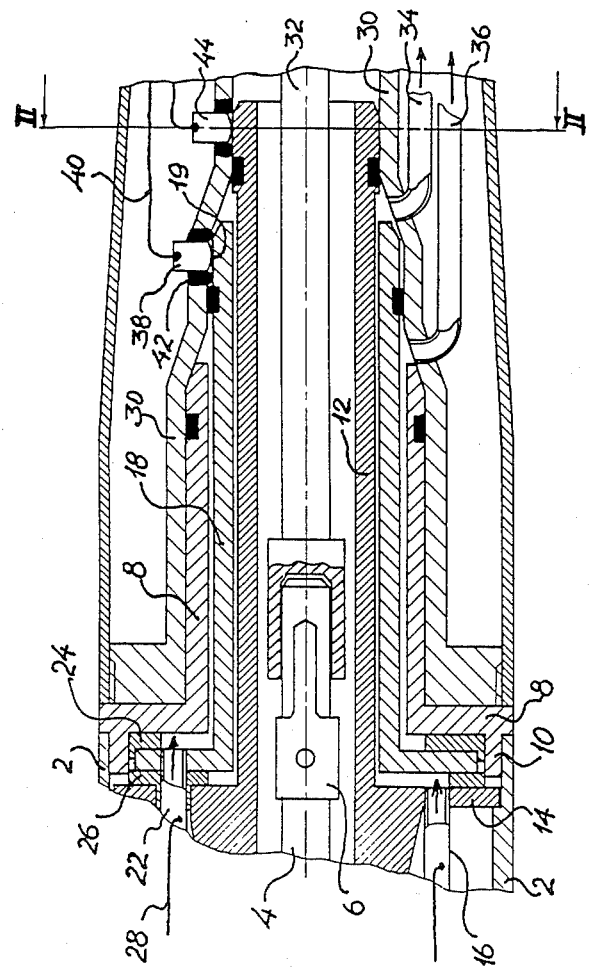

United States Patent [19]

Goof

[11] Patent Number: 4,732,563
[45] Date of Patent: Mar. 22, 1988

[54] POWER UNIT, IN PARTICULAR FOR DENTAL INSTRUMENTS, AND TOOL UNIT FOR USE IN CONNECTION WITH SUCH POWER UNIT

[76] Inventor: Sven K. L. Goof, 236 A, Gl. Strandvej,, DK-3050 Humlebak, Denmark

[21] Appl. No.: 849,681
[22] PCT Filed: Aug. 13, 1985
[86] PCT No.: PCT/DK85/00078
   § 371 Date: Apr. 9, 1986
   § 102(e) Date: Apr. 9, 1986
[87] PCT Pub. No.: WO86/01094
   PCT Pub. Date: Feb. 27, 1986

[30] Foreign Application Priority Data
Aug. 14, 1984 [DK] Denmark ............... 3899/84

[51] Int. Cl.⁴ .................................. A61C 1/00
[52] U.S. Cl. ........................... 433/29; 433/82
[58] Field of Search ............ 433/126, 29, 85, 82

[56] References Cited
U.S. PATENT DOCUMENTS
4,568,284 2/1968 Stanklewicz .............. 433/126

Primary Examiner—Robert Peshock
Attorney, Agent, or Firm—Tilton, Fallon, Lungmus

[57] ABSTRACT

A power unit, in particular for dental instruments, comprises a housing (2) which, at one end, has means for supplying electric current and at least one fluid, and, at the other end, has a connector branch or stub for removably mounting a tool unit thereon. The connector stub includes an interior partition wall (18) which defines flow passages for transfer of fluid through the connector stub. This partition wall is in electrically conducting connection (28) with the current supply means, and the partition wall (18) is electrically insulated or separated from the remaining walls of the connector stub. The partition wall (18) has a contact face (19) which is accessible from the exterior of the stub.

A tool unit includes a coupling socket with an interior wall (30) for insertion on the connector stub. A contact (38) is mounted in the interior wall (30) and is adapted to provide connection with the contact face (19), when the tool unit is in place on the connector stub. Thereby it is possible to transfer fluids as well as electric current to a tool, without the removability of the tool unit giving rise to complications.

6 Claims, 5 Drawing Figures

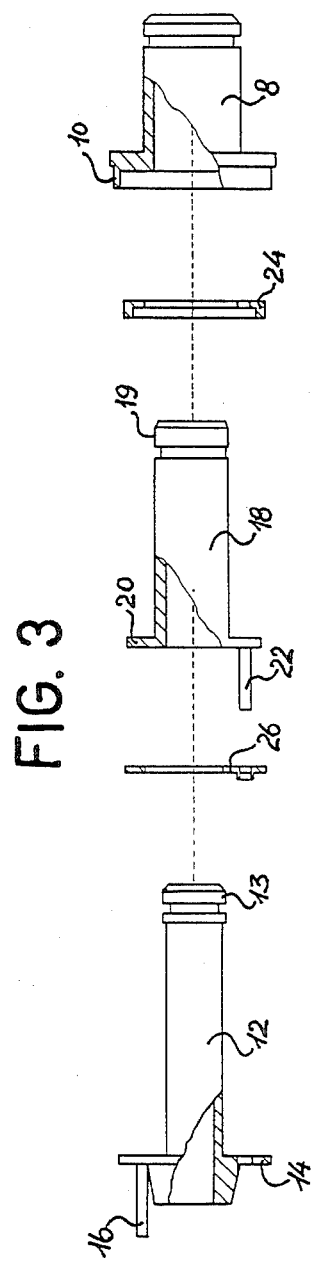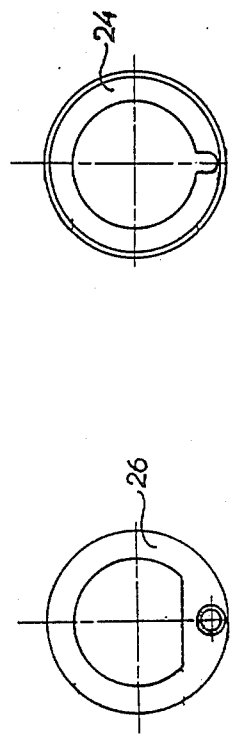

POWER UNIT, IN PARTICULAR FOR DENTAL INSTRUMENTS, AND TOOL UNIT FOR USE IN CONNECTION WITH SUCH POWER UNIT

The present invention relates to a power or drive unit, in particular for dental instruments and to a tool unit connectable to such a power unit, in which passages are provided therethrough the power unit for transmitting electricity and one or more fluids to the tool unit. Power units of the general type are used in particular for dental drills, but can also be used for drills or cutters, for example, for use in connection with surgical operations.

In the case of a drilling or cutting instrument, the housing of the power unit contains a motor which may be either an electric motor or a turbine. The motor drives an output shaft which extends centrally in the coupling stub of the power unit and is, usually, terminated by an appropriate self-catching clutch part which is adapted to engage a matching clutch part in a tool unit, when the tool unit is being put into place on the connector stub. At the same time as the tool unit is being put into place, communication is established between fluid flow passages in the connector stub and corresponding flow passages in the tool unit, whereby fluids, such as water and air, are transfered and can be supplied to the work site of the tool unit through appropriate outlets or nozzles.

Instruments or appliances of this type are known in the art, wherein replacable tool units are designed with a small lamp for illuminating the work site during use of the tool. Due to the restricted space, in particular through the connector stub of the power unit, it has, however, been a problem to have electric current carried through to such a lamp. Therefor it has been attempted to arrange a map at the rear end of the power unit i.e. opposite the connector stub, and to conduct light from this lamp to a light source on the tool unit, whereby the light is transfered through a light conductor in the shape of one or more light conducting fibres which extend through the housing or handle portion of the power unit and on to the light source on the tool unit. Danish patent publication No. 146 647 discloses an example of such a known instrument.

However, in a power unit for removable or replacable tool units such an arrangement of light conductors is not useful without further measures. Moreover, it is necessary to install such a light conductor in an appropriate passage which, at least though the connector stub of the power unit, has to be made as an axially extending bore. The drilling of such a bore is very difficult to make with sufficient precision, in particular in view of the fact that it is necessary to drill relatively long distances axially through small wall thicknesses of material which, usually, is stainless steel and therefor is relatively hard.

In accordance with the invention one or more of the passage-defining walls in the connector stub is utilized as an electric conductor. Consequently, it is possible to transfer not only fluids, such as water and/or air, but also electric current to a removable or replacable tool unit without any need of drilling bores axially through walls in the connector stub.

The power unit of the invention does not necessarily include a motor or turbine, since the unit can be used as drive unit for replacable spraying or flushing tools with a lamp, and/or as power unit for a removable curing lamp for composite tooth filler materials. In the latter case it is an advantage that the tool unit which is designed as a curing lamp, can be cooled interiorly by means of the power unit of the invention, because know curing lamps tend to be hot during use to such an extent that they become unpleasant to hold in the hand.

However, a prefered embodiment of this invention includes a motor or turbine with a drive shaft which is arranged centrally in the connector stub. Thus, with this embodiment it is possible to transfer mechanical driving power, at least two fluid flows as well as electric current to replacable tool units.

As will be understood from the statements above, the tool unit can be designed for instance as a flushing tool with built-in light source; as a radiation supplying tool with interior cooling; or as a usual drilling or cutting tool with cooling and/or flushing medias and with supply of light to the work site.

Figure 2:
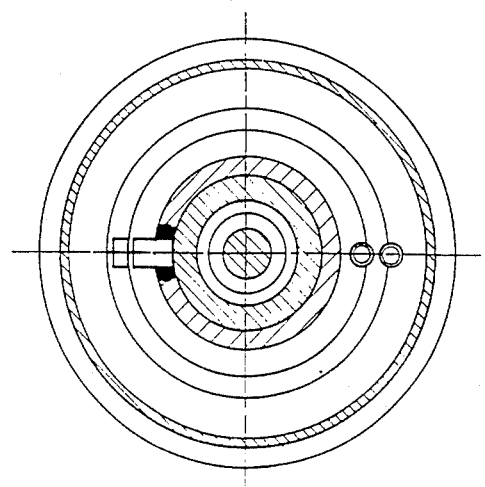

The invention will now be described in further detail with reference to the drawings in which FIG. 1 schematically shows a partial axial section through a power unit in accordance with the invention with a tool unit of the invention mounted thereon, FIG. 2 is a sectional view taken along 2—2 in FIG. 1, FIG. 3 is an exploded view showing tubular bushings and interposed electrically insulating ring elements which are parts of the connector stub of the power unit in FIG. 1, FIGS. 4 and 5 are plan views showing the respective insulating ring elements.

The drive or power unit of the invention shown in FIG. 1 comprises a housing 2 which contains a motor (not shown) driving an output shaft 4, the end of the shaft having a self-catching clutch part 6. The output or drive shaft 4 is supported in such a manner that the clutch part 6 is located centrally in the interior of a hollow connector branch or stub, which is assembled by concentrically arranged and tubular bushings which are tightened or clamped axially on one end of the housing 2 by means of an outermost stub bushing 8 which has a threaded flange 10 for threadingly engaging the housing 2.

The connector stub further comprises an innermost stub bushing 12 which at one end thereof has a mounting flange 14 which carries a pipe 16 extending therethrough. The connector stub also comprises a midmost stub bushing 18 also having a mounting flange 20 with a pipe 22 extending therethrough.

Between the flange 10 on the outermost stub bushing 8 and the mounting flange 20 on the midmost stub bushing 18, there is inserted a first electrically insulating ring element 24. Similarly, a second electrically insulating ring element 26 is inserted between the mounting flange 20 of the midmost stub bushing 18 and the stub bushing 14 of the innermost stub bushing 12.

By means of these electrically insulating ring elements 24, 26 the midmost bushing 18 is electrically insulated or separated from the remaining bushings 8, 12, when the three bushings are slid into each other as shown in FIG. 1. In that connection the pipe 22 will be guided through corresponding openings in the ring element 26 and in the mounting flange 14 of the innermost bushing 12. As will appear, in particular from FIGS. 3 and 4, the ring element 26 is shaped and designed in such a manner that the pipe 22 is kept electrically separated from the opening in the flange 14.

The ring elements 24, 26 also operate as spacers and centering means so that the three stub bushings 8, 18 and 12 are retained coaxially relative to each other and thereby define respective intermediate annular flow passages. The pipe 16 communicates with the flow passage defined between the innermost and the midmost stub bushings, and, similarly, the pipe 22 communicates with the flow passage defined between the midmost and outermost stub bushings.

By means of a system of tubes or flow passages (not shown) in the interior of the housing 2, it is, consequently, possible to introduce for example water through the pipe 22, and for example air through the pipe 16, such fluids being supplied in usual manner through respective supply means at the opposite and not shown end of the housing 2.

Simultaneously, the pipe 22 can be utilized as electrical terminal, whereby an electric potential can be applied to the midmost bushing 18 from electric supply means in the housing 2, as indicated schematically at 28 in FIG. 1.

At the distal, free end of the connector stub, the lengths of the three bushings are stepped-down in such a manner that the innermost bushing 12 is the longest. Thus, the distal or outer end portion of each of the bushings is accessible from the outside, and the distal or outer end portion of the midmost bushing 18 is designed as an electric contact face 19, preferably a circumferential slide contact path. If desired, also the distal or outer end portion of the innermost bushing may be designed as an electric contact face 13 in a similar manner.

FIG. 1 shows, moreover, a part of a tool unit in accordance with the invention which has been slid onto the connector stub of the power unit. The tool unit has a coupling socket with an interior wall or surface 30 having a shape which is adapted to the outer surface of the connector stub, so that the socket can be slipped axially onto the connector stub.

In the embodiment shown, the coupling socket supports a shaft 32 which extends to a tool (not shown), such as a drill. With the socket slipped in place on the connector stub, i.e. primarily on the outermost bushing 8 thereof, the clutch-part on the shaft 32 is engaged with the clutch part 6 on the drive shaft 4 of the power unit. Appropriately, a suitable releasable snap-lock may be arranged between the stub bushing 8 and the socket of the tool unit in order to retain the tool unit properly in place and in engagement. However, the socket, and thereby the entire tool unit, should preferably be rotatable on the connector stub of the power unit.

The interior wall 30 of the coupling socket also supports two pipes or conduits 34, 36 which receive fluid from the respective annular flow passages defined in the connector stub of the power unit. These pipes may lead to suitable outlets or nozzles which are directed towards the work site of the tool.

On the interior wall 30 there is, moreover, arranged a contact face which in the embodiment shown, is designed as a slide contact 38 having one end in contact with the contact face 19 and the other end being connected with an electric wire 40. The slide contact 38 is electrically separated from the interior wall 30, and preferably the slide contact 38 is embedded in a resilient and electrically insulating material 42. Thereby it is possible to provide an elastic biasing of the slide contact 38 against the contact face 19 on the connector stub.

Through the wire 40 a voltage or electric potential on the stub bushing 18 can be transfered for use at needs in the tool unit, for example for powering a lamp which may be adapted to illuminate the work site of the tool.

In order to ensure an effective electric return path, it may be appropriate to provide a similar contact face or slide contact 44 which is in engagement with the distal end portion 13 of the innermost stub bushing 12. The electric return path or frame connection is thereby ensured from the tool unit and back to the current terminals in the housing 2 of the power unit.

With an embodiment as that shown in the drawings, it is accordingly possible to transfer mechanical drive power to a tool, and, at the same time, two fluids as well as electric current can be transfered to the tool, without the replacability of the tool giving rise to substantial complications as far as manufacture and use are concerned.

I claim:

1. A power unit for a hand-held instrument, such as a dental handpiece, comprising an elongate housing equipped with means for transmitting electrical current and at least one fluid therethrough, and provided at one end with connector stub means for removably connecting a tool unit to said power unit; said connector stub means having walls including longitudinal partitions defining passages for the flow of fluid through the interior of said connector stub means; wherein the improvement comprises at least one of said longitudinal partitions of said connector stub means being formed of electrically conductive material and being adapted for connection to a source of electrical current; said one partition being electrically isolated from other walls of said connector stub means and including a laterally-directed externally-exposed contact face for establishing electrical connection with a corresponding contact face of a tool unit connectable to said power unit.

2. A power unit in accordance with claim 1, wherein said housing includes a motor or turbine and has means for transmitting two or more fluids, and wherein said connector stub means comprises a longitudinally-extending drive shaft adapted for engagement with a driven shaft of a tool unit; said power unit having a plurality of said longitudinal partitions in the shape of radially-spaced coaxially-arranged tubular bushings defining annular fluid passages therebetween; each bushing having a mounting flange thereon; annular electrical insulating elements disposed between said mounting flanges; and means securing said mounting flanges and insulating elements against said housing.

3. A power unit in accordance with claim 2, in which each contact face thereof is shaped as a circumferential contact surface at the distal end of one of said tubular bushings; the lengths of the respective coaxial tubular bushings being reduced in steps as reckoned from the innermost bushing to the outermost bushing.

4. A tool unit for use in connection with a power unit as defined in claims 1, 2, or 3 comprising coupling socket means adapted to receive said connector stub means of said power unit; said coupling socket means having an interior wall with a surface shape which is complementary to the outer surface of said connector stub means; said interior wall providing at least one contact face electrically isolated from the remainder of said coupling socket means and connected to an electric wire; said contact face of said socket means defining said corresponding contact face for establishing electrical connection with said contact face of said connector stub means.

5. A tool unit in accordance with claim 4, wherein each contact face of said interior wall of said socket means comprises a sliding contact member for slidably engaging one of said laterally-directed contact faces of said connector stub means along a circumferential contact path.

6. A tool unit in accordance with claim 5 in which said sliding contact member includes a generally radially-extending contact pin embedded in a resilient and electrically-insulating material that biases said pin towards, and into engagement with, one of said laterally-directed contact faces of said connector stub means.

* * * * *